United States Patent

Barnes

(10) Patent No.: US 9,162,061 B2
(45) Date of Patent: Oct. 20, 2015

(54) VISION ENHANCEMENT FOR A VISION IMPAIRED USER

(75) Inventor: Nick Barnes, Canberra (AU)

(73) Assignee: NATIONAL ICT AUSTRALIA LIMITED, Eveleigh, NSW (AU)

( * ) Notice: Subject to any disclaimer, the term of this patent is extended or adjusted under 35 U.S.C. 154(b) by 770 days.

(21) Appl. No.: 13/500,606

(22) PCT Filed: Oct. 7, 2010

(86) PCT No.: PCT/AU2010/001320
§ 371 (c)(1),
(2), (4) Date: May 24, 2012

(87) PCT Pub. No.: WO2011/041842
PCT Pub. Date: Apr. 14, 2011

(65) Prior Publication Data
US 2012/0242801 A1    Sep. 27, 2012

(30) Foreign Application Priority Data

Oct. 9, 2009   (AU) ................................ 2009904959

(51) Int. Cl.
*A61N 1/36*   (2006.01)

(52) U.S. Cl.
CPC .......... *A61N 1/36046* (2013.01); *A61N 1/3606* (2013.01); *A61N 1/36128* (2013.01)

(58) Field of Classification Search
CPC ............ A61H 3/06; A61H 3/061; A61F 9/08; A61N 1/36046
See application file for complete search history.

(56) References Cited

U.S. PATENT DOCUMENTS

| | | | |
|---|---|---|---|
| 3,654,477 A | | 4/1972 | Benjamin, Jr. |
| 5,728,156 A | * | 3/1998 | Gupta et al. ................. 623/6.26 |
| 6,298,010 B1 | | 10/2001 | Ritz et al. |
| 6,658,299 B1 | | 12/2003 | Dobelle |
| 7,308,314 B2 | * | 12/2007 | Havey et al. .................... 607/54 |
| 2002/0105514 A1 | * | 8/2002 | Roche, Jr. ..................... 345/419 |
| 2002/0138264 A1 | | 9/2002 | Janakiraman et al. |
| 2002/0159629 A1 | | 10/2002 | Dutta et al. |
| 2004/0030383 A1 | | 2/2004 | Havey et al. |
| 2005/0015120 A1 | * | 1/2005 | Seibel et al. .................... 607/54 |
| 2007/0016425 A1 | * | 1/2007 | Ward ............................ 704/271 |
| 2007/0055336 A1 | * | 3/2007 | Greenberg et al. .......... 607/141 |
| 2008/0309913 A1 | * | 12/2008 | Fallon ......................... 356/4.01 |
| 2010/0220176 A1 | | 9/2010 | Ziemeck et al. |

FOREIGN PATENT DOCUMENTS

| | | |
|---|---|---|
| GB | 2 376 397 | 11/2002 |
| WO | 03/107039 | 12/2003 |

OTHER PUBLICATIONS

European Search Report, Appl. No. 10821484.2, Issue date: May 10, 2013; 4 pages.

* cited by examiner

*Primary Examiner* — Sath V Perungavoor
*Assistant Examiner* — Nathnael Aynalem

(57) ABSTRACT

This invention concerns a vision enhancement apparatus that improves vision for a vision-impaired user of interface equipment. Interface equipment stimulates the user's cortex, directly or indirectly, to provide artificial vision. It may include a passive sensor to acquire real-time high resolution video data representing the vicinity of the user. A sight processor to receive the acquired high resolution data and automatically: Analyze the high resolution data to extract depth of field information concerning objects of interest. Extract lower resolution data representing the vicinity of the user. And, provide both the depth of field information concerning objects of interest and the lower resolution data representing the vicinity of the user to the interface equipment to stimulate artificial vision for the user.

16 Claims, 4 Drawing Sheets

| 100 | 5 | 5 | 100 |
|-----|-----|-----|-----|
| 100 | 5 | 5 | 100 |
| 100 | 5 | 5 | 100 |
| 100 | 100 | 5 | 100 |

FIG. 4

VISION ENHANCEMENT FOR A VISION IMPAIRED USER

TECHNICAL FIELD

This invention concerns a vision enhancement apparatus that improves vision for a vision-impaired user of interface equipment. Interface equipment stimulates the user's cortex, directly or indirectly, to provide artificial vision. It may include a bionic eye, retinal implant, optic nerve cuff, optic nerve penetrating array, cortical implant or vision spectacles. In further aspects the invention concerns a method for enhancing vision, and software to perform the method.

BACKGROUND ART

Many 'blind' people have partial sight of one kind or another. For instance cataracts cause sight to dim across the entire field of vision, but retinitis pigmentosa can produce tunnel vision where all peripheral vision is lost. Age related macular degeneration (AMD) causes the opposite effect, where the central region of vision becomes obscured but the peripheral vision is still available.

DISCLOSURE OF THE INVENTION

In a first aspect, the invention is vision enhancement apparatus for a vision-impaired user of interface equipment, comprising:
A passive sensor to acquire real-time high resolution video data representing the vicinity of the user.
A sight processor to receive the acquired high resolution data and automatically:
Analyse the high resolution data to extract depth of field information concerning objects of interest.
Extract lower resolution data representing the vicinity of the user.
And, provide both the depth of field information concerning objects of interest and the lower resolution data representing the vicinity of the user to the interface equipment to stimulate artificial vision for the user.

As a result of the invention, a user of interface equipment will have, for instance, real-time depth of field information about detected objects presented to them visually in a manner, where the information can be interpreted for ambulatory navigation around obstacles.

The passive sensor may be a video image camera in which case it captures a series of video images. The depth of field information concerning objects of interest may be derived from the video images by any convenient means of image analysis. The resulting depth of field information may then be inserted into the video data.

In general the low resolution data representing the vicinity of the user is obtained from the high resolution data by down sampling. This may include any depth of field data that has been inserted into the video data. The combined data also provides a richer representation of a visual scene to the user. For instance the user may see the depth of field information presented visually as a depth map, such as a cylindrical, radial or spherical grid over their field of vision. Within that depth map objects of interest could be coloured or highlighted in some way. Alternatively, hazard warnings could be presented.

The depth of field could alternatively be presented by a light or colour appearing, in the user's field of view, which they are taught to interpret. For instance a particular colour spot appearing at the bottom of the field of view could indicate a trip obstacle ahead. It will be appreciated that the user is not necessarily seeing what is before them in the field of view of the camera but, like a fighter pilot, is seeing a virtual head up display which they are trained to interpret.

Other possibilities include animated warnings that change depending on the relative speed or direction, or both, between the user and the object. For instance, a 'time to contact' alert in the form of a map. In general 'time to contact is the relative distance between the user and the object divided by the relative velocity toward the object. Such a hazard warning might usefully be enhanced by the addition of an audible beat that increases in frequency as the distance between the user and obstacle decreases.

Specific visual hazard warnings may be provided depending on the user's activity. For instance a common hazard faced by visually impaired people when walking is collision with tree branches that overhang the footpath. The invention can be configured to provide hazard warnings in the event of detecting overhanging branches or other obstacles ahead.

A pair of video cameras may be used to provide a pair of stereoscopic signals, for respective eyes. These images may be analysed in real time, for instance using triangulation techniques, to extract depth of field information in the form of distance information from the user to objects of interest.

The objects of interest may include the ground in front of the user, the walls of buildings and obstacles, such as furniture, trees, kerbs, and the like. If the vision enhancement apparatus is provided with data representing the height of the user, then head height obstacles, such as overhanging branches, may also be identified as objects of interest.

It should be appreciated that objects of interest include objects that might not be in the field of view of a normal sighted person. For instance the sensors may be directed toward acquiring data about obstacles on the ground.

Where user has some remaining retinal function the interface equipment will typically comprise a 'visual display array' that operates to stimulate the remaining retinal function; for example a bionic eye, retinal implant or vision spectacles.

In the case the interface equipment is a pair of vision spectacles, enhanced images are presented in front of the users eyes to stimulate the light receptors in the retina. In the case the interface equipment is a retina implant, data is applied directly to the retina to stimulate it electrically.

In cases where the user has an area of retina remaining with high image resolution, the visual display array is used to stimulate that area; for instance in the case of a user suffering from retinitis pigmentosa.

User's with lower vision capabilities may have the visual display array presented in some other area of their remaining vision; for instance a user suffering from macular degeneration may have the array presented in their peripheral vision.

Where part of the retina does not function, the images may be reordered so that the information about detected objects is directed to a functioning part of the retina.

Users with lesser vision may have the artificial vision stimulated by a cortical or pre-cortical implant. In this case the depth of field information concerning objects of interest may be presented to the user may stimulating the production of phosphenes in the cortex that convey information; such as colours or flashing lights. Or course, such informational signals may also be provided by a visual display array.

In another example, a vision-impaired user who wishes to cycle may not be able to see obstacles such as bollards and letter boxes, and the system could be configured to provide warnings about these obstacles Of course the apparatus is not only useful for identifying obstacles that are to be avoided, but also for people and things that the user wishes to find or make contact with.

In a second aspect, the invention is a method for enhancing the vision of a vision-impaired user of interface equipment, comprising the steps of:
Acquiring real-time depth of field data about the vicinity of the user.
Automatically using the acquired data to stimulate the user's retina via the interface equipment.

In a further aspect the invention is software for performing the method.

BRIEF DESCRIPTION OF THE DRAWINGS

An example of the invention will now be described with reference to the accompanying drawings, in which:
FIG. 4 is an image of an alternative type of image presented to the user.

BEST MODES OF THE INVENTION

Figure 1:
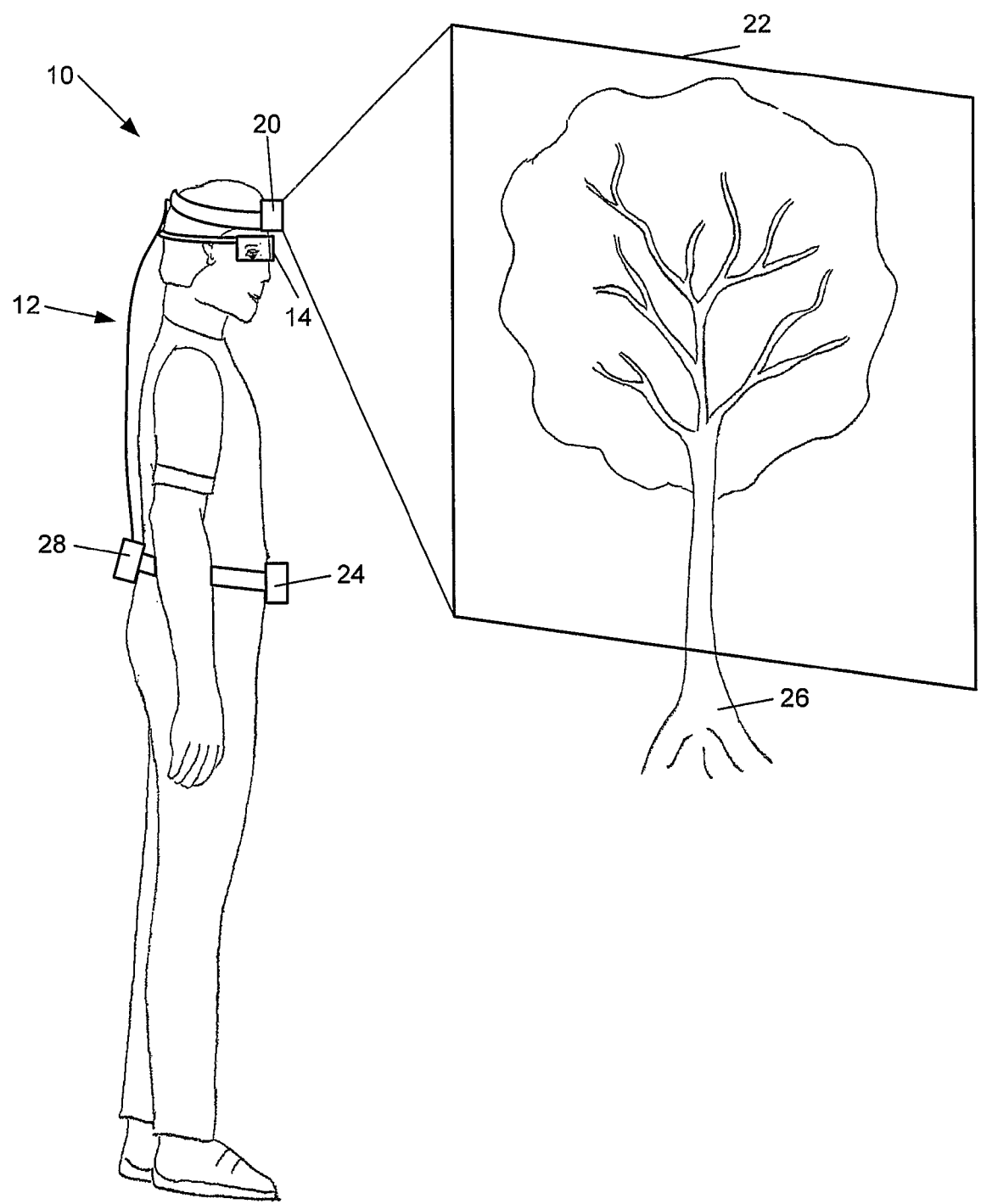
FIG. 1 is a block diagram of vision enhancement apparatus.

Referring first to FIG. 1, the vision enhancement apparatus 10 supports a vision-impaired user 12 of interface equipment 14, such as vision spectacles that provide a stereoscopic image to the user's eyes. The apparatus 10 comprises a video camera 20 is mounted on the user's head that operates to acquire video data representing scenes 22 in the vicinity of the user 12.

Figure 3:
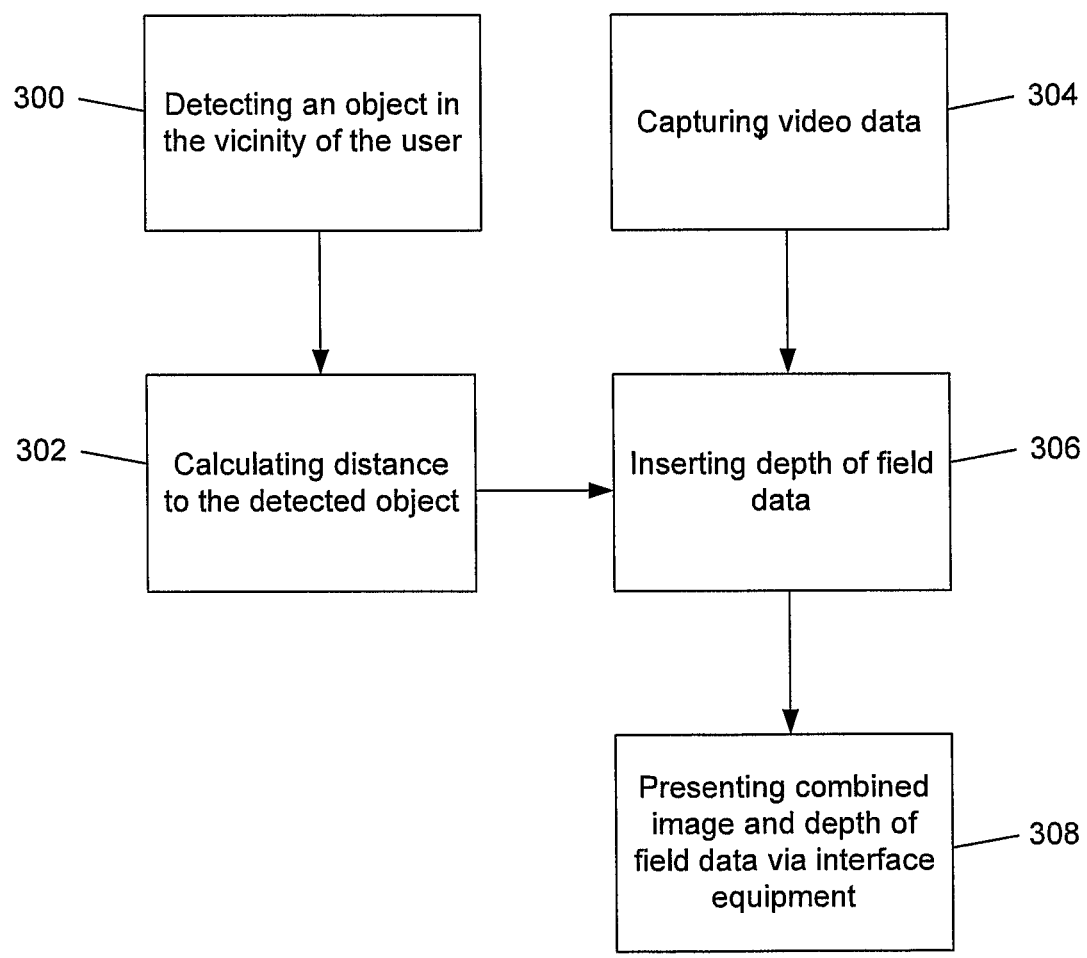
FIG. 3 is flowchart of the process for delivering the depth of field information into the users view.

An object detection system 24 is also mounted on the user's waistband acquires object data about objects, such as tree 26 in the vicinity of the user [step 300 in FIG. 3]. In particular the object detection system 24 determines how far the tree 26 is from the user 12 [step 302 in FIG. 3]. This is achieved by simple reflection of ultrasonic transmissions emanating from the system 24 from the tree 26, and calculating the transit time.

Part of tree 26 is also in the scene 22 filmed by the video camera 20 [step 304 in FIG. 3].

The sight processor 28 is also mounted on the user's waistband to receive video data from camera 20 and object data from object detection system 24. The sight processor uses the distance information between the user and the tree to automatically insert real-time depth of field information about the detected tree into the video data [step 306 in FIG. 3]. This information will then be visually presented to the user by means of the vision spectacles 14 [step 308 in FIG. 3]. The camera 20, vision spectacles 14, object detection system 24 and image processor 28 are all interconnected by wires, as shown; or wirelessly by a personal area network (PAN).

Figure 2:
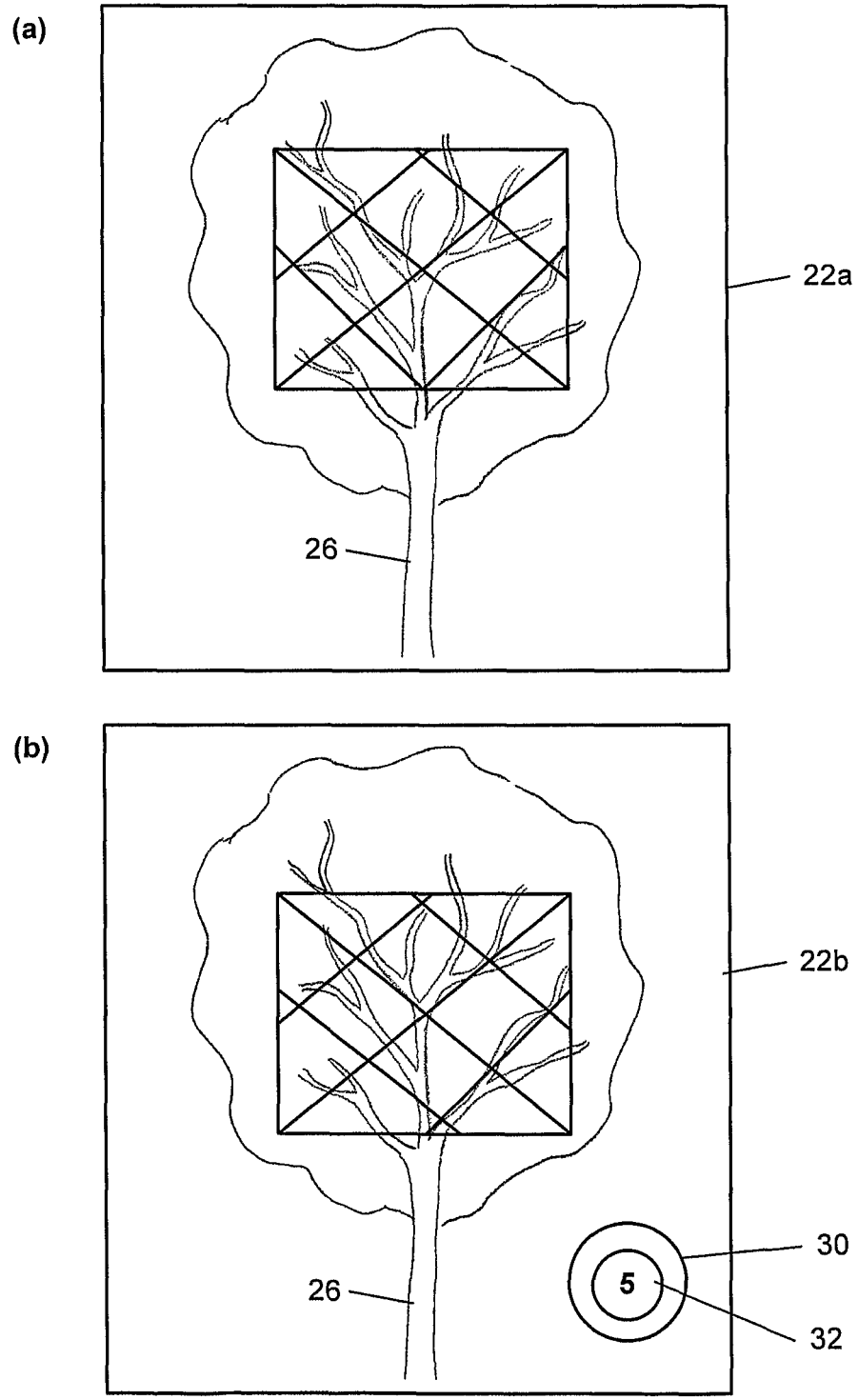
FIG. 2 is a pair of images showing:
(a) The user's natural view of a scene.
(b) The user's view with a depth of field information included.

In this case the user 12 has macular degeneration so their vision is obscured in the central region; as shown in FIG. 2(a) where almost all the foliage of the tree is obscured when user 12 looks directly at it from this distance.

The image presented to the user is enhanced by the sight processor 28. In this case the tree 26 is detected by the object detection system 24, and the tree 26 is the only object detected. As a result, the object detection system 24 sends data to the sight processor indicating the distance of the user from the tree.

In this case both the user 12 and tree 26 are stationary, so the sight processor 28 includes a target 30 in the bottom right of the image displayed to the user. In the centre of target 30 is the encircled number '5' 32; as shown in FIG. 2(b). This indicates to the user 12, in part of the image they can see and read, that the tree is directly in front of them and 5 meters away.

The direction of the tree 26 is indicated by the position of the number 32 in the target 30; that is central=directly ahead. And, the distance is given by the number '5'.

In the event the user 12 was walking forward, directly towards the tree 26, then the number 32 would be continually flashing—indicating change—and the number 32 would count down as the distance decreased.

It should be appreciated that the direction and distance information, in this case, is completely independent of the image of the tree 26 being shown to the user 12, since the user 12 could be pointing the camera 20 in another direction entirely and the image being shown in the vision spectacles could be of something else. However, the direction and distance information would remain unchanged, since the object detection system 24 is mounted on the user's waistband.

In an alternative arrangement, the depth of field sensor is in the form of a non-visual depth sensing array, such as a large array of high resolution millimeter wave radar, or a 3D laser scanner, which generates a field of data representing distance measures that can be mapped into a grid by the sight processor 28.

In this case, data acquired by the depth of field sensor can be used directly to stimulate the user's retina, without having to acquire any video data. For example, for a retinal implant or a bionic eye having between 100 and 1000 actual visual fields (roughly pixel equivalent), the sight processor 28 can render the depth of field data directly as intensity on a 100 electrode array of the retinal implant or bionic eye. A pair of field sensors may also be used to provide a pair of stereoscopic signals, for respective eyes.

Figure 4:
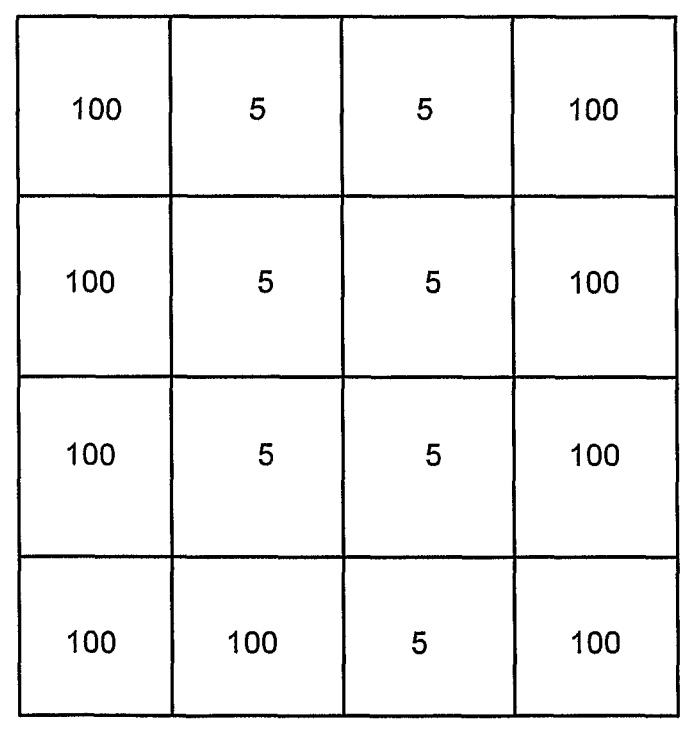

One exemplary mode involves the sight processor 28 computing dense stereo depth across a field at high resolution, then taking a minimum depth value over each cell in the field, and applying that minimum value as a maximum to the cells of the interface equipment 14. In practice, the absolute maximum value of each cell may be too error prone, and therefore the minimum is smoothed over a small region to increase robustness. Such a grid can then be presented to the user via the interface equipment 14, so that the user 12 sees an image as shown in FIG. 4. In this case, cells having value '5' represent an object that is 5 meters away while '100' represents no obstacles within 100 meters from the user 12.

Although the invention has been described with reference to a simple example, it will readily be appreciated that far more sophisticated examples could be constructed. For instance object detection could be performed in many different ways, including by analysis of the video data. The presentation of the depth of field information could also be achieved in many different ways; for instance using a light, brightness or colour, moving graphics or other techniques.

Also, the ground plane could be represented in the depth data by fitting a horizontal plane, and this can then be used to map distances parallel to the ground between the observer and an object. A phosphene could then be used to represent just the horizontal component of the distance from the observer to an object. This may be particularly useful if the resolution is very low, such as less than one hundred elements. Here each visual element could be used as a polar histogram of object distances. With more visual elements, each one could simply map the horizontal distance to the nearest object over its field of view, and then the elements are providing cylindrical coordinates. A gravity sensor or inertial navigation system could be used to assist plane fitting by estimating the direction of the ground plane.

The invention claimed is:

1. Vision enhancement apparatus for a vision-impaired user of interface equipment, comprising:
    a passive sensor to acquire real-time high resolution data representing the vicinity of the user; and
    a sight processor to receive the acquired high resolution data and automatically analyse the high resolution data to extract depth of field information concerning objects of interest, extract lower resolution data representing the vicinity of the user and provide both the depth of field information concerning objects of interest and the lower resolution data representing the vicinity of the user of the interface equipment to directly or indirectly stimulate the user's cortex to provide artificial vision of the depth of field information and the low resolution data for the user.

2. Vision enhancement apparatus according to claim 1, wherein the passive sensor is a video image camera that captures a series of video images, and the depth of field information concerning objects of interest is derived from the captured video images.

3. Vision enhancement apparatus according to claim 2, wherein the resulting depth of field information is inserted into the video data.

4. Vision enhancement apparatus according to claim 1, wherein the low resolution data representing the vicinity of the user is obtained from the high resolution data by down sampling.

5. Vision enhancement apparatus according to claim 3, wherein the user sees the depth of field information presented visually as a depth map.

6. Vision enhancement apparatus according to claim 5 wherein the depth of field map is a cylindrical, radial or spherical grid over their field of vision.

7. Vision enhancement apparatus according to claim 5, wherein the depth map colours or highlights objects of interest.

8. Vision enhancement apparatus according to claim 1, wherein depth of field information is conveyed as an indication of 'time to contact'.

9. Vision enhancement apparatus according to claim 1, wherein a pair of video cameras are used to provide a pair of stereoscopic signals, for respective eyes, and these images are analysed in real time, using triangulation techniques, to extract depth of field information in the form of distance information from the user to objects of interest.

10. Vision enhancement apparatus according to claim 1, wherein the user has some remaining retinal function and the interface equipment comprises a 'visual display array' that operates to stimulate the remaining retinal function.

11. Vision enhancement apparatus according to claim 10, wherein the user has an area of retina remaining with high image resolution, and the visual display array is used to stimulate that area.

12. Vision enhancement apparatus according to claim 10, wherein where part of the retina does not function, the images are reordered so that the information about detected objects is directed to a functioning part of the retina.

13. Vision enhancement apparatus according to claim 1, wherein users with little or no retinal function have artificial vision stimulated by a cortical or pre-cortical implant.

14. Vision enhancement apparatus according to claim 13, wherein the depth of field information concerning objects of interest is presented to the user by stimulating the production of phosphenes in the cortex that convey information.

15. A method for enhancing the vision of a vision-impaired user of interface equipment, comprising the steps of:
    acquiring real-time high resolution video data representing the vicinity of the user;
    analysing the high resolution data to extract depth of field information concerning objects of interest;
    extracting lower resolution data representing the vicinity of the user; and
    providing both the depth of field information concerning objects of interest and the lower resolution data representing the vicinity of the user of the interface equipment to directly or indirectly stimulate the users cortex to provide artificial vision of the depth of field information and the lower resolution data for the user.

16. A non-transitory computer readable medium with an executable program stored therein that when executed causes a computer to perform the method of claim 15.

* * * * *